United States Patent [19]
Gitis et al.

[11] Patent Number: 5,795,990
[45] Date of Patent: Aug. 18, 1998

[54] METHOD AND APPARATUS FOR MEASURING FRICTION AND WEAR CHARACTERISTICS OF MATERIALS

[75] Inventors: Norm Gitis, Cupertino; Leo Levinson, Mountain View; Vlad Dorfman, Mountain View; Michael Vinogradov, Mountain View, all of Calif.

[73] Assignee: Center for TriBology, Inc., Mountain View, Calif.

[21] Appl. No.: 902,728

[22] Filed: Jul. 30, 1997

[51] Int. Cl.⁶ .............................. G01N 3/56; G01N 19/02
[52] U.S. Cl. .......................................... 73/9; 73/10
[58] Field of Search ................................ 73/9, 10

[56] References Cited

U.S. PATENT DOCUMENTS

| | | | |
|---|---|---|---|
| 3,372,574 | 3/1968 | Armour et al. | 73/9 |
| 4,939,922 | 7/1990 | Smalley | 73/9 |
| 4,958,511 | 9/1990 | Marcus | 73/7 |
| 4,966,030 | 10/1990 | Kobayashi | 73/7 |
| 5,315,860 | 5/1994 | Dreilich | 73/9 |
| 5,377,525 | 1/1995 | Hutchinson | 73/9 |
| 5,679,883 | 10/1997 | Wedeven | 73/10 |

FOREIGN PATENT DOCUMENTS

| | | | |
|---|---|---|---|
| 2277342 | 1/1976 | France | 73/10 |
| 242486 | 9/1969 | U.S.S.R. | 73/10 |

OTHER PUBLICATIONS

An article "Stick–Slip and Machine Tools" by Wolf G.J. (Lubric. Eng. 1965, vol. 21, N7, p. 273).

Primary Examiner—Hezron E. Williams
Assistant Examiner—Daniel S. Larkin
Attorney, Agent, or Firm—Ilya Zborovsky

[57] ABSTRACT

A tester of the invention has a horizontal base with a vertical column that supports vertical guides for guiding a carriage that supports a rotary drive mechanism for an upper specimen which is secured in a chuck and engages a lower specimen supported by an interchangeable bowl. The tester is also provided with a computerized measuring system for precisely measuring characteristics to be tested. The main distinguishing feature of the tester of the invention is a that a flexible coupling that may have at least one degree of freedom (preferably three) is installed in a link between a rotary motion unit and the chuck for fixing the upper specimen. In other words, the upper specimen is fixed in a self-aligning manner so that its flat working surface is always maintained in full surface-to-surface contact with the lower specimen. In addition, a provision of the flexible coupling in the link between the drive unit and the zone of friction contact makes it possible to decrease strictness in requirement of manufacturing accuracy of guides and other parts of the tester.

14 Claims, 7 Drawing Sheets

5,795,990

1

METHOD AND APPARATUS FOR MEASURING FRICTION AND WEAR CHARACTERISTICS OF MATERIALS

FIELD OF THE INVENTION

The present invention relates to the field of tribology and, more particularly, to a method and apparatus for measuring friction and wear characteristics of materials.

BACKGROUND OF THE INVENTION

Tribology is a science of friction, wear, and lubrication on friction surfaces. Many different types of testers, tribometers, and other devices for measuring various parameters of friction and wear processes are known in the art. These parameters are mainly a coefficient of friction, static and dynamic friction forces, friction torque, adhesion force, abrasion and adhesion wear on the sliding surfaces, etc.

U.S. Pat. No. 5,377,525 issued in 1995 to John M. Hutchinson describes a test apparatus for carrying out analysis on fluids or components comprising two specimens which are moveable with respect to each other by means of an oscillating driving mechanism such as an electromagnetic vibrator. A measurable load is applied between the both specimens. The oscillating driving mechanism has a stiffness adjusting device, utilized for controlling the degree of lateral movement of the oscillating mechanism. The tester is also provided with a force measuring device which is connected to a support. In order to achieve accurate results of the measurements, the support is much heavier than both the oscillating driving mechanism and the specimens.

Since this apparatus provides only an oscillating driving motion, it has a very limited and specific application.

U.S. Pat. No. 5,315,860 issued in 1994 to L. Dreilich et al. discloses a device for measuring a coefficient of friction depending on the relative speed between samples and a brake disk. Two samples are pressed to friction surfaces on opposite sides of a brake disk with a predetermined force. A force with which the samples are dragged transversely to the pressing force is measured during the testing as a function of time and speed.

The Dreilich tester also is very specific and is applicable to testing brake disks only.

Similarly, many other devices and testers relating to the field of tribology have very specific purpose and are intended mainly for testing concrete products or type of products.

Thus, U.S. Pat. No. 4,966,030 issued in 1990 to T. Kobayashi discloses a pinon-disk type wear testing device which measures only wear of the specimens without testing any other parameters of a friction process.

U.S. Pat. No. 4,958,511 issued in 1990 to Leon Marcus discloses a method and apparatus for wear testing of anodized surfaces and, therefore, is applicable to electrically conductive materials only. This apparatus is not suitable for measuring coefficient of friction.

A relatively universal machine, that examines sliding friction between exposed surfaces of different combinations of materials participating in a friction process with lubricants tested under different temperature conditions, is described in U.S. Pat. No. 4,939,922 issued to R. Smalley et al. in 1990. However, this device like all other testers mentioned above is not sufficiently universal and sensitive and involves the use of a complicated cam mechanism and elevated temporaries to cause a substantial change of energy in testing.

2

Low measurement sensitivity of the existing friction and wear testers is a reason these testers are not applicable for measuring stick-slip characteristics of a friction pair. Stick-slip is a phenomenon of an intermittent movement on sliding parts at low feeding speeds caused by friction.

Stick-slip phenomena measurement is described in an article entitled "Stick-Slip and Machine Tools" by Wolf G. J. (Lubric. Eng. 1965, Vol. 21, N7, P. 273). The device, disclosed in this article, measures stick-slip by manually reading indicator values and collecting the data for static and kinetic friction. The apparatus is applicable only to flat samples, and its data is fully dependent on operator's skills. The device lacks flexibility of setting different velocities. Furthermore, the load is applied by a calibrated spring which is applicable for loads only in a limited range.

Thus, none of the existing testers is universal enough to provide measurements of a coefficient of friction, friction torque, friction force, abrasive wear of the specimens, friction characteristics of thread, friction characteristics under cold and hot conditions, and stick-slip characteristics on one tester.

Another disadvantage of conventional testers is that they do not provide high rigidity in transmitting a torque to a specimen and thus unable to compensate for angular misalignment between specimens during the test.

Still another disadvantage of conventional testers is that they are not sufficiently sensitive to displacements of specimens in the axial direction.

None of the existing testers for friction measurements that involves the use of two specimens having flat contact ensures full contact over the entire working surface. For example, if an end face of a rod-like specimen contacts flat surface of a disk, in order to ensure full surface-to-surface contact, the tester should have extremely high manufacturing accuracy in parts that determine positioning of one specimen to the other.

OBJECTS AND SUMMARY OF THE INVENTION

It is an object of the invention to provide a universal tester for testing coefficient of friction, friction torque, friction force, abrasive wear of the specimens, friction characteristics of thread, friction characteristics under cold and hot conditions, and stick-slip characteristics on one tester.

Another object is to provide a tester for testing aforementioned parameters in specimens of different types, configurations, and materials.

Still another object is to provide a tester capable of measuring characteristics of a stick-slip phenomena.

Another object is to provide a tester that ensures full surface-to-surface contact of flat specimens.

Further object is to provide a tester that is relatively inexpensive to manufacture.

Another object of the invention is to provide a method of testing a coefficient of friction, friction torque, friction force, abrasive wear of the specimens, friction characteristics of thread, friction characteristics under cold and hot conditions, and stick-slip characteristics on one tester with high rigidity in transmitting a torque in combination with high sensitivity to axial displacements of the specimen.

Further object is to provide a tester that possesses high rigidity in transmitting a torque in combination with high sensitivity to axial displacements of the specimen.

In general, the tester of the invention consists of a horizontal base with a vertical column that supports vertical

3 guides for guiding a carriage that supports a rotary drive mechanism for an upper specimen, which is secured in a chuck and engages a lower specimen supported by an interchangeable bowl. The tester is also provided with a computerized measuring system for precisely measuring characteristics to be tested. The main distinguishing feature of the tester of the invention is a that a flexible coupling that may have at least one degree of freedom (preferably three) is installed in a link between a rotary motion unit and a chuck for fixing the upper specimen. In other words, the upper specimen is fixed in a self-aligning manner, so that its flat working surface is always maintained in full surface-to-surface contact with the lower specimen. In addition, a provision of the flexible coupling the link between the drive and the zone of friction contact makes it possible to decrease the strictness in requirement of manufacturing accuracy of guides and other parts of the tester.

These and other features and advantages of the invention will become more apparent after the consideration of the ensuing description with the attached drawings.

DETAILED DESCRIPTION OF THE INVENTION

Figure 1:
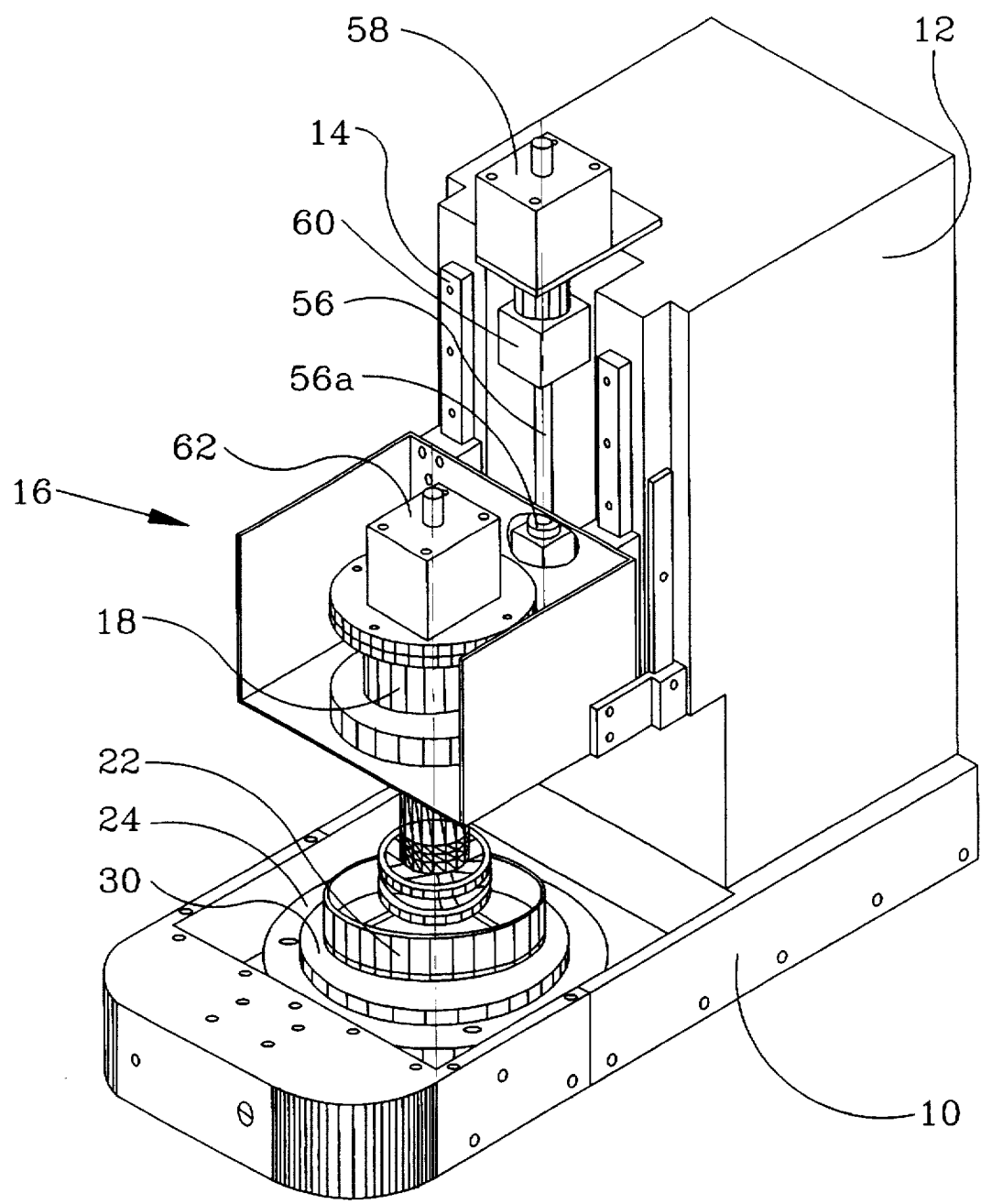
FIG. 1 is a general three-dimensional view of the tester of the present invention.
Figure 2:
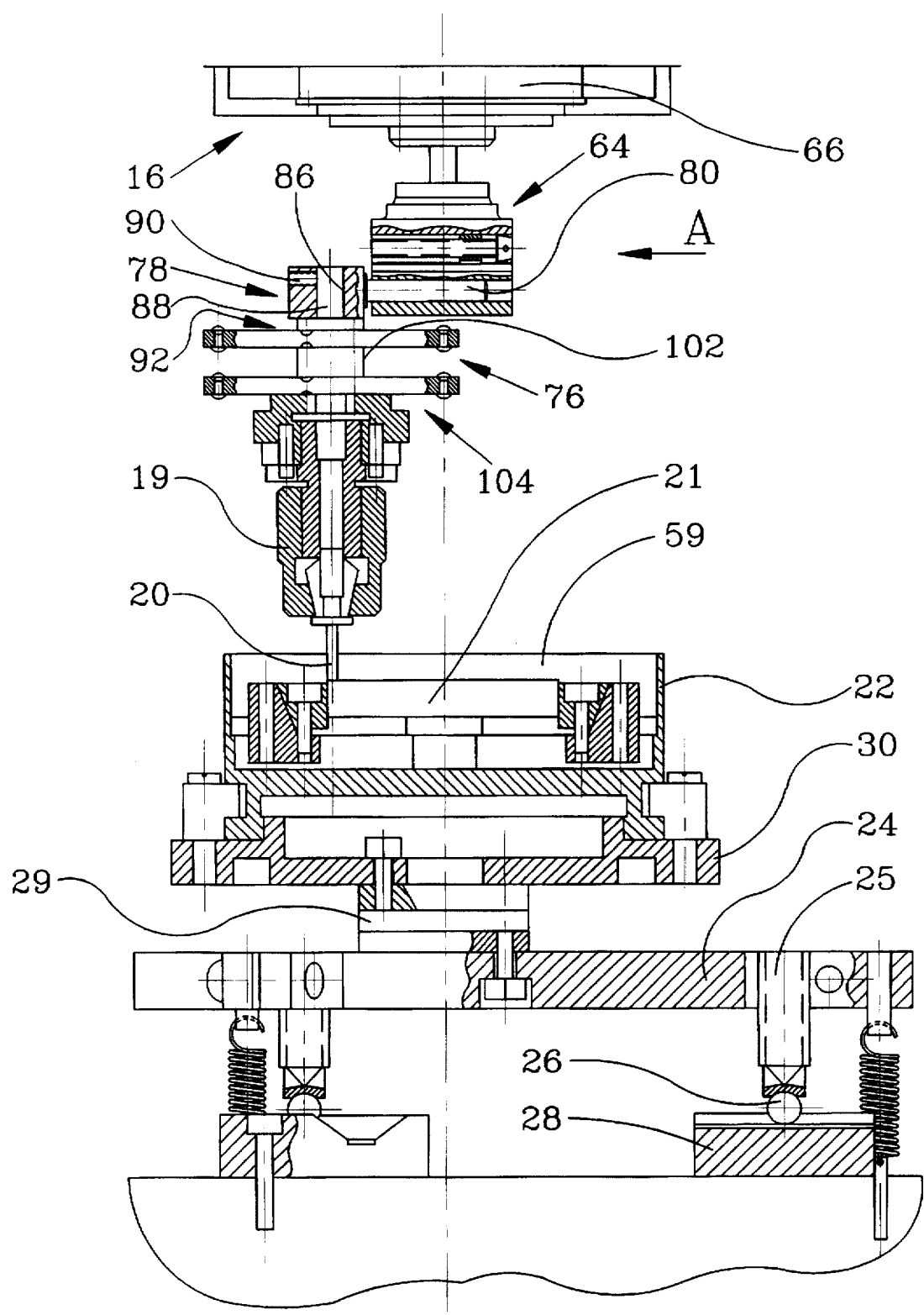
FIG. 2 is a fragmental vertical partially-sectional view of the tester of FIG. 1.

A three-dimensional view of the tester of the invention is shown in FIG. 1. FIG. 2 is a vertical partially-sectional view of the tester of FIG. 1. In general, the tester consists of a rigid stationary frame in the form of a horizontal base 10 with a vertical column 12 that supports vertical guides 14 for guiding a carriage 16 that supports a rotary drive mechanism 18 for an upper specimen 20 (FIG. 2), which is secured in a chuck 19 and engages a lower specimen 21 supported by an interchangeable bowl 22. Chuck 19 may be in the form of a conventional collet-type chuck convenient for clamping rod-like specimens. The tester is also provided with a computerized measuring system 23 for precisely measuring characteristics to be tested.

Now the aforementioned main units of the tester of the invention will be described in more detail each.

Base 10 is made of a solid heavy material, such as metal or stone, to ensure stability of the parts supported by the base. When it may be or should be necessary, base 10 may be made as a rigid hollow box-like structure that is fixed to a stationary bench or table.

Base 10 supports a lower plate 24 (FIG. 2) by means of three equally angularity spaced balls 26 on three prisms 28 spaced equally in a circumferential direction (only two of these prisms are shown in FIG. 2). Precise leveling of lower plate 24 in horizontal plane is carried out with the use of three screws 25 threaded into lower plate 24 and supporting aforementioned balls 26 at the points of contact with prisms 28. Lower plate 24 supports an intermediate plate 30 which, in turn, supports aforementioned bowl 22. A sensor, e.g., a load cell 29 is placed between lower plate 24 and intermediate plate 30 for measuring a friction force and friction torque developed during testing between upper specimen 20 and lower specimen 21. This sensor may be a standard device such as Mini 20/1 produced by Assurance Technologies Inc., Garner, N.C., USA.

Figure 3:
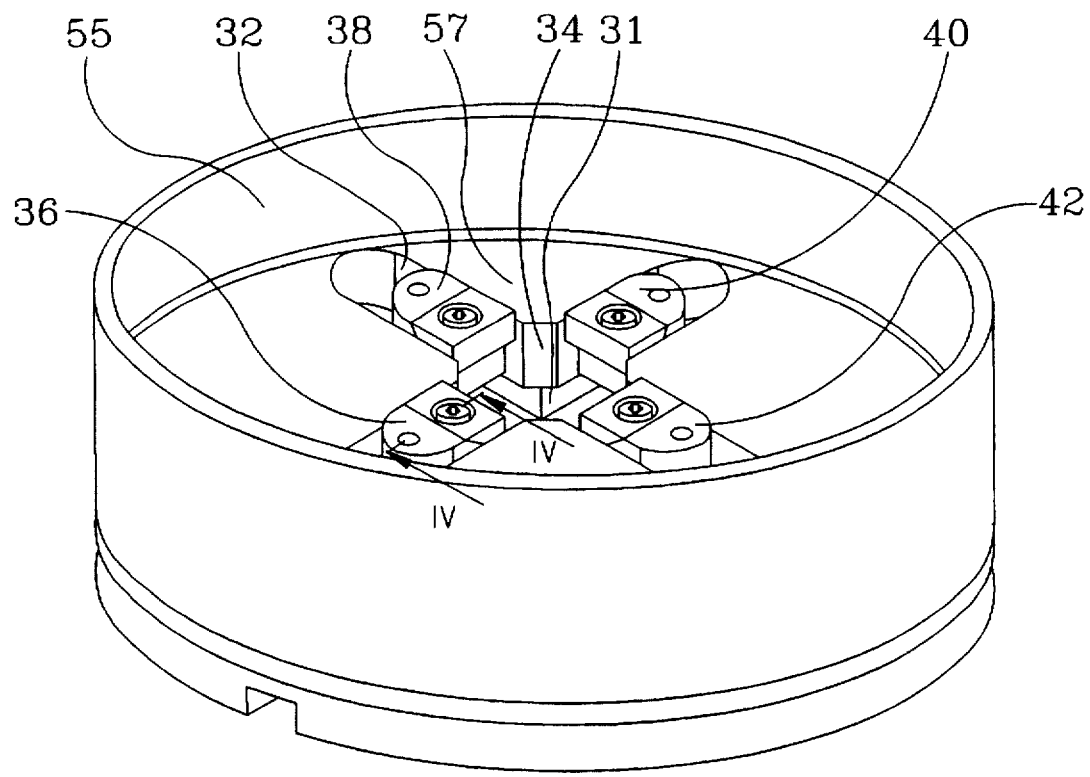
FIG. 3 is a three-dimensional view of an interchangeable for supporting the lower specimen.
Figure 4:
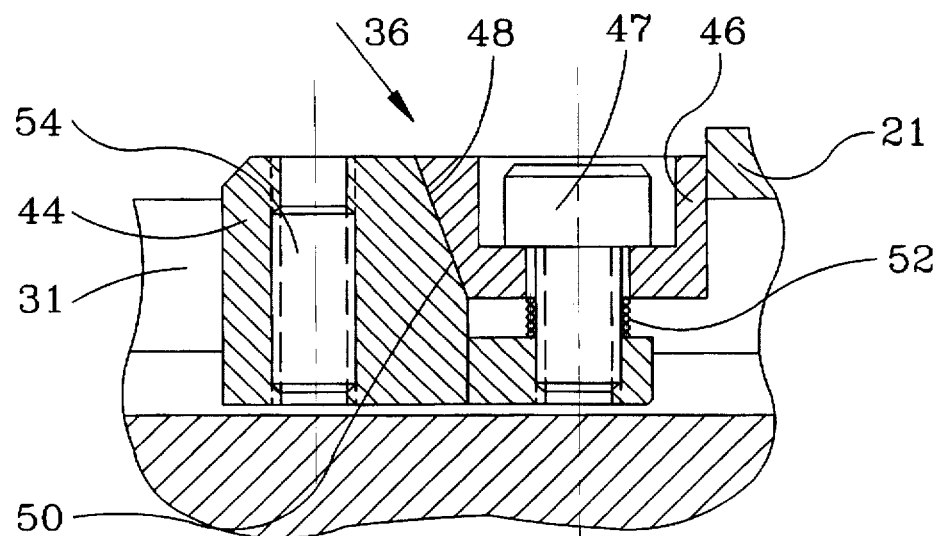
FIG. 4 is a fragmental sectional view along line IV—IV of FIG. 3 illustrating the construction of the clamping sliders for the fixation of the lower specimen.

The construction of bowl 22 is shown in more detail in FIGS. 3 and 4, where FIG. 3 is a three-dimensional view of a bowl for supporting the lower specimen, and FIG. 4 is a fragmental sectional view along line IV—IV of FIG. 3 illustrating the construction of the clamping sliders for the fixation of the lower specimen.

As can be seen from these drawings, bowl 22 comprises a cylindrical body with two diametrical slots 31 and 32 that intersect in the center of bowl 22, thus forming a space 34 for rod-like specimens (not shown). Slots 31 and 32 have a T-shaped cross section for receiving T-shaped clamping sliders 36, 38, 40, and 42. Since all clamping sliders are identical, only one of them, i.e., clamping slider 36 will be described with reference to FIG. 4. As shown in FIG. 4, slider 36 consists of two parts, i.e., a slider block 44 and a wedging member 46. Slider block 44 has a T-shaped lower portion, which is slidingly guided in a respective T-shaped slot. In its upper part, slider block 44 has a wedging surface 48 which engages a wedging surface 50 of wedging member 46. The latter is resiliently urged to slider block by flexible means such as a spring 52. Wedging member 46 is connected to slider block 44 by a screw 47. Each clamping slider is fixed in a selected position in bowl 22 by means of a clamping screw 54. Upper edge 55 of the bowl periphery is raised above a flat upper surface 57 to form a cavity 59 (FIG. 2), which can be filled with oil for testing specimens under lubricating conditions.

When clamping screw 54 is screwed into slider block 44 and comes into contact with the bottom of T-slot of the bowl 22, it is shifted up and is pressed against the upper wall of a respective T-slot, thus fixing the clamping slider in the selected position. The final clamping of lower specimen 21 is performed by tightening screws 47, thus causing wedging member 46 to move radially inwardly and, hence, clamping the lower specimen.

Carriage 16 is guided along vertical guides 14 by means of a lead screw 56 driven by a stepper motor 58 for linear movements. Lead screw 56 is supported in a bearing unit 60. Lead screw 56 engages a nut 56a which is rigidly secured to the back side of carriage 16, so that rotation of lead screw 56 controlled by stepper motor 58 causes vertical movement of carriage 16 along vertical guides 14.

Figure 5:
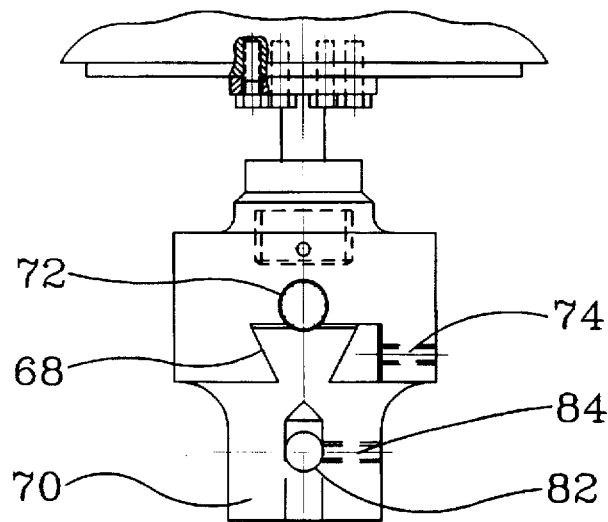
FIG. 5 is a fragmental view in the direction of arrow A in FIG. 2.

As shown in FIG. 2, carriage 16 supports a rotary stepper motor 62 (FIG. 1) that rotates an upper specimen holder 64 via a reducer 66. Upper specimen holder 64 is strictly coaxial with the center of bowl 22 and has a radial guiding slot 68 which is shown in FIG. 5. FIG. 5 is a fragmental view of holder 64 in the direction of arrow A in FIG. 2. Slot 68 serves for guiding a slider 70, the position of which can be adjusted by means of a micrometric screw 72 and is fixed in the adjusted position by a screw 74.

Upper specimen holder 64 supports collet chuck 19 that holds upper specimen 20 by means of a coupling 76 which is an essential feature of the present invention and will be described in detail below. Coupling 76 is supported in upper specimen holder 64 by means of an angular adapter 78 which has a horizontal axle 80 inserted into an opening 82 (FIG. 5) of slider 70. Adapter 78 is fixed in slider 70 by means of a screw 84. Angular adapter 78 has a vertical opening 86 which is parallel to the axis of rotation of upper specimen holder 64. Vertical opening 86 serves for the fixation of an input member 88 of coupling 76 locked in adapter 78 by means of a screw 90.

Figure 6:
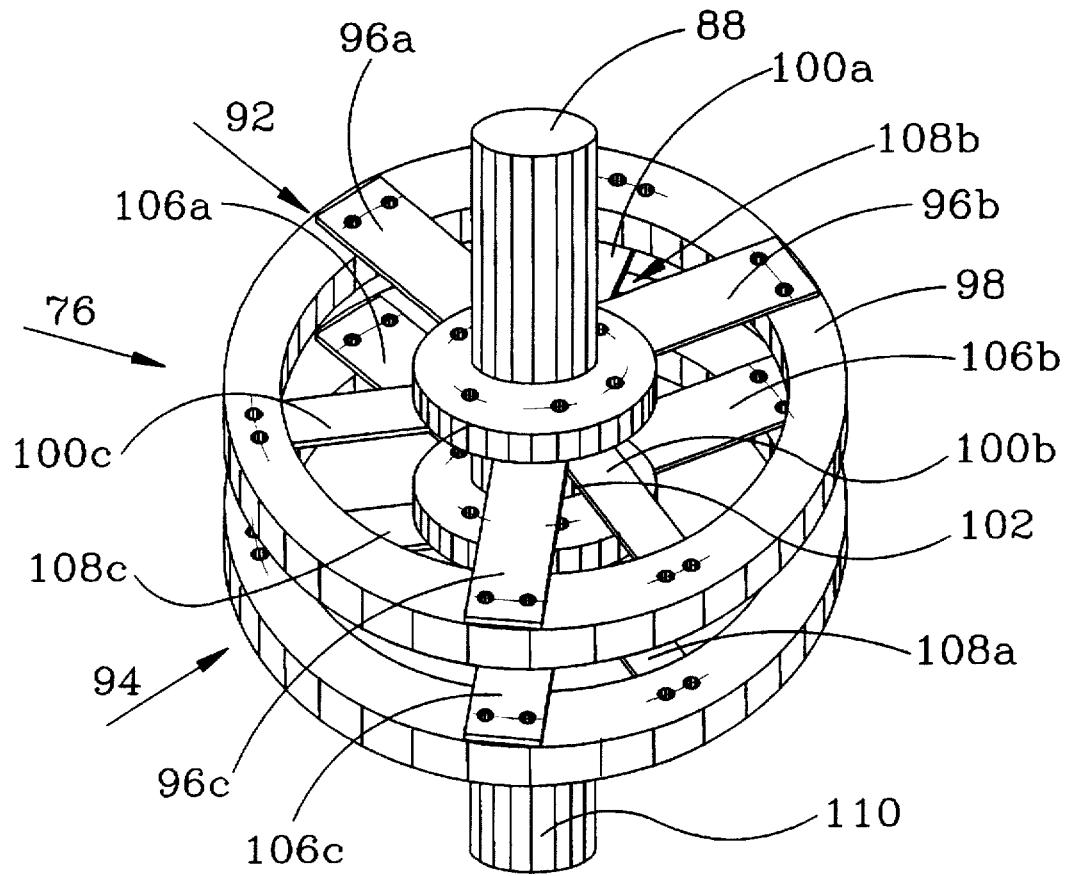
FIG. 6 is a three-dimensional view of a double-row spring flexure coupling for stick-slip measurements and for compensating misalignment of the specimens, the coupling having three-degrees of freedom.

A three-dimensional view of double-row spring flexure coupling 76 for stick-slip measurements, for rigidity in the torque-transmitting direction, and for compensating angular misalignments of vertical axes of the specimens is shown in FIG. 6.

In the embodiment shown in FIG. 6, coupling 76 has three degrees of freedom. This coupling consists of an upper half-coupling 92 and a lower half-coupling 94. Input member 88 of upper half-coupling 92 is supported by three leaf springs 96a, 96b, and 96c. Each leaf spring extends radially from the upper side of peripheral portion 98 of upper half-coupling 92 toward the central part of upper half-coupling 92, where it is attached to input member 88.

Another set of leaf springs 100a, 100b, and 100c is located on the lower side of upper half-coupling 92. Springs 100a, 100b, and 100c extend each from the lower side of peripheral portion 98 of upper half-coupling 92 toward the central part of the upper half-coupling 92 where it is attached to the upper end of a spacer 102 (FIG. 2). The lower end of spacer 102 is attached to a lower half-coupling 104. The latter has the same construction as upper half-coupling 92, with the exception that the upper set of radial leaf springs 106a, 106b, and 106c are attached to the upper end of spacer 102 and that the lower set of radial springs 108a, 108b, and 108c support an output member 110 of coupling 76.

In other words, input member 88 is rigidly fixed in adapter 78 and rotates from stepper motor 62 (FIG. 1), whereas output member 110 and hence upper specimen 20 has three degrees of freedom with respect to input member 88. These degrees of freedom are the following: an axial movement in the direction of the vertical axis Z (which ensures measurement of the stick-slip phenomenon), compensatory angular displacements in the direction of axis X, and compensatory angular displacements in the direction of axis Y (which compensates for non-parallelity of contact surfaces of both specimens).

Thus, the purpose of coupling 76 is to transmit a torque to upper specimen 20 and a measurement force from upper specimen 20 to lower specimen 21 with compensation of non-parallelity of contact surfaces of the specimens. As a result, the contact surfaces of the specimens will always be in full contact with each other.

A coupling of the type shown in FIG. 6 may be suitable for testing under conditions without strict requirements with regard to parallelity of axes of both specimens. For those tests where parallelity of the axes of upper and lower specimens is a critical issue, for example, in testing of threaded specimens where nonparallelity may generate undesired lateral components of the force, a coupling of the type shown in FIGS. 7 and 8 may be advantageous.

Figure 7:
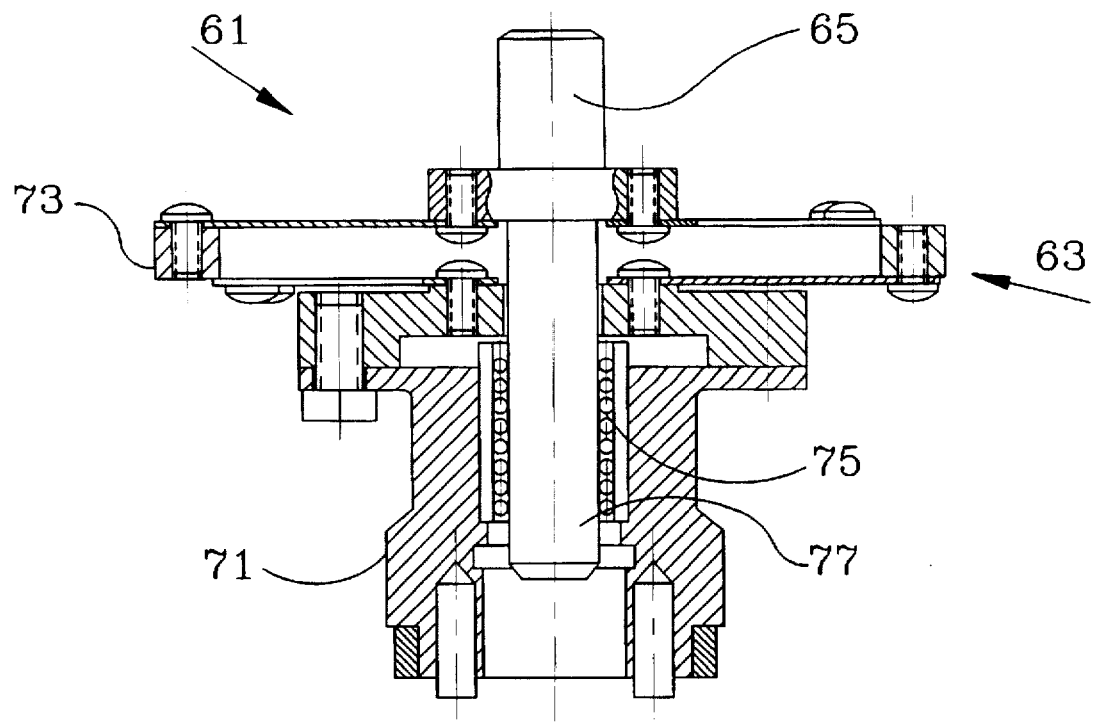
FIG. 7 is a sectional side view of a single-row spring flexure coupling having degree of freedom only in the axial direction.
Figure 8:
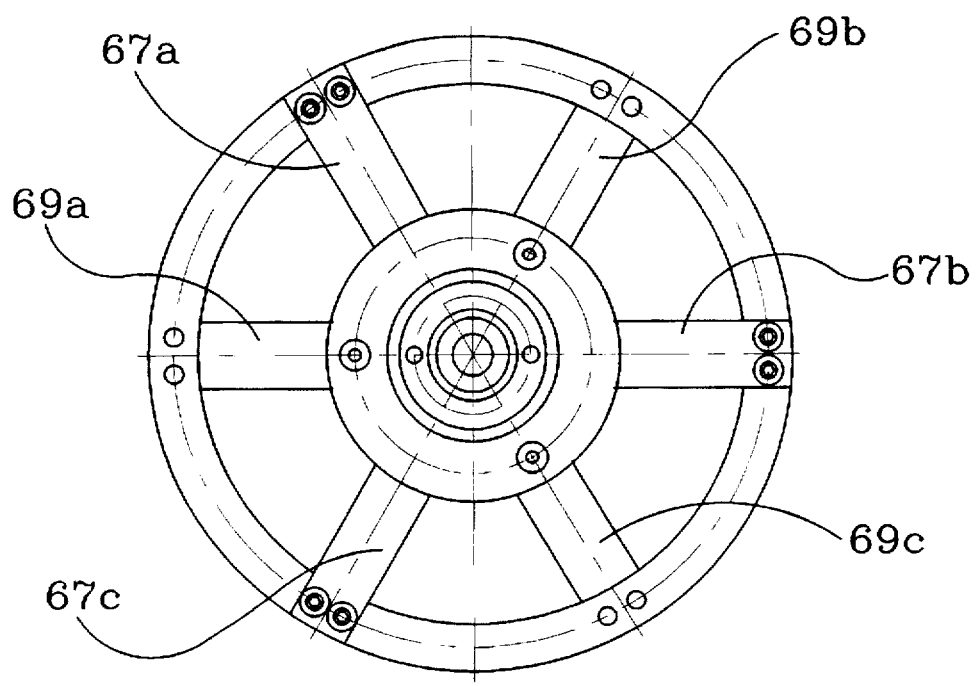
FIG. 8 is a bottom view of the coupling of FIG. 7.

FIGS. 7 and 8 are side and bottom views of a single-row spring flexure coupling. This coupling, which can be installed in the tester instead of the coupling of FIG. 6, has only one degree of freedom, i.e., only in the axial direction. In general, a single-row coupling 61 is similar to the one shown in FIG. 6 and differs from it in that it has only one disk 63. An input member 65 of the coupling is attached to the output member of reducer 66 in the same manner as input member 88 of the double-row coupling and is connected to an output member 71 of the coupling by two sets of leaf springs 67a, 67b, 67c and 69a, 69b, 69c. A spacer 73 is placed between both sets of springs in order to provide a space between them for freedom of relative axial motion, but with angular rigidity in the direction of transmission of the torque from input member 65 to output member 71.

In order to ensure strict coaxiality between input member 65 and output member 71 and hence parallelity of axes of the upper specimen and the lower specimen (in FIGS. 7 and 8 both specimens are not shown), output member 71 supports a linear ball bearing 75 strictly coaxial with the pilot end 77 of input member 65. Since rigid pilot portion 77 is inserted into output member 71 without backlash, output member is kept strictly aligned with the input member and cannot be slanted with respect thereto.

Figure 9:
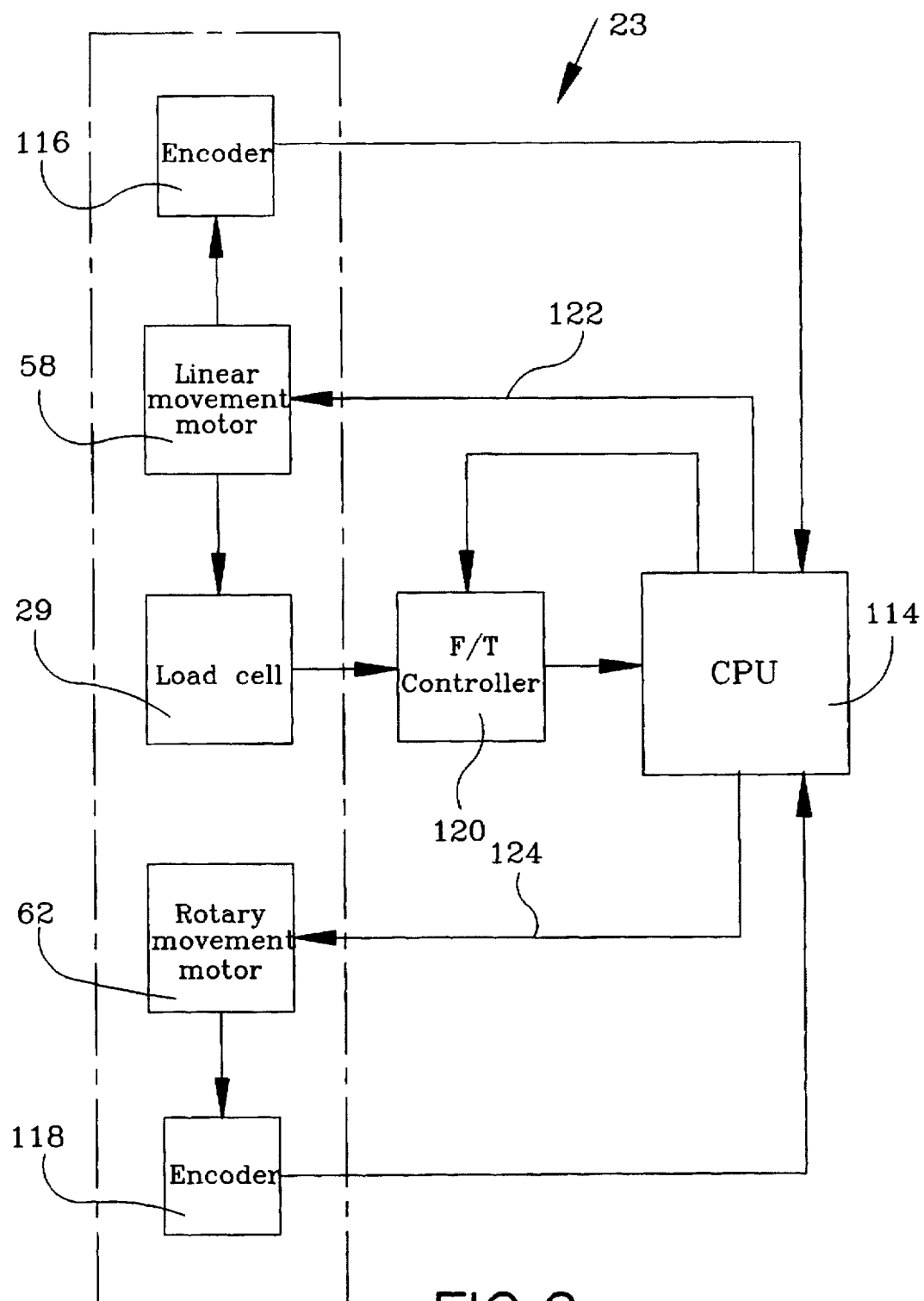
FIG. 9 is a block diagram of the measurement system of the apparatus of the invention.

The measurement system of the apparatus of the invention is shown in a block-diagram form in FIG. 9. The system consists of a CPU in the form of a computer 114, stepper motors 58 and 62 with respective encoders 116 and 118, respectively. Linear motion motor 58 is connected to computer 114 via load cell 29 and a friction force/torque controller 120. Computer 114 is connected to motors 58 and 62 via feedback circuits 122 and 124, respectively.

OPERATION OF THE TESTER

The operation of the tester will be first considered in conjunction with the double-row coupling of FIG. 6.

Prior to testing, upper specimen 20 is inserted into chuck 19 and is securely clamped in it. Lower specimen is then placed into bowl 22. In FIG. 2 lower specimen 21 is shown in the form of a disk. Lower specimen 21 is placed on flat surface 57 and is clamped by means of T-shaped clamping sliders 36, 38, 40, and 42 that slide in respective T-shaped slots 31 and 32. Clamping is carried out in two stages. First lower specimen 21 is leveled on the flat horizontal surface 57, clamping sliders 36, 38, 40 and 42 are brought in contact with the periphery of the lower specimen, and each clamping slider is fixed in a selected position by means of a clamping screw 54. Final clamping of the lower specimen is performed by tightening respective screws 47 which produces a wedging action and moves members 46 radially inwardly thus clamping the lower specimen in place.

If testing has to be conducted under lubricating conditions, cavity 59 is filled with oil.

Stepper motor 58 is switched on and this causes rotation of lead screw 56 and hence vertical movement of carriage 16 along vertical guides 14. When upper specimen 20, which moves down together with carriage 16, comes into contact with the working surface of lower specimen 21, this moment is detected by load cell 29 and is registered by CPU 114. The latter one sends a stopping signal via feedback circuit 122 to motor 58. Load cell is reset to zero. Due to a provision of flexible coupling 76 which, as described above, has three degrees of freedom, the contact surfaces of both specimens will always have full surface-to-surface contact as a result of self-alignment of upper specimen 20. In addition, a provision of the flexible coupling the link between the drive and the zone of friction contact makes it possible to decrease strictness in requirement of manufacturing accuracy of guides and other parts of the tester.

The test is then initiated by switching motor 62 on for rotation which is transmitted via reducer 66 to lower specimen 20. During testing, measurement system measures and registers the parameters of testing. Depending on the type of testing, the following parameters can be measured: a coefficient of friction, friction torque, friction force, abrasive wear of the specimens, friction characteristics of thread (in case of threaded specimens), friction characteristics under cold and hot conditions, in case of a bowl with a heater chamber (not shown), and stick-slip characteristics.

Stick slip characteristics can be measured by detecting moments of friction sticking and by measuring the force and torque at which the sticking is overcome and relative movement is resumed.

Figure 10:
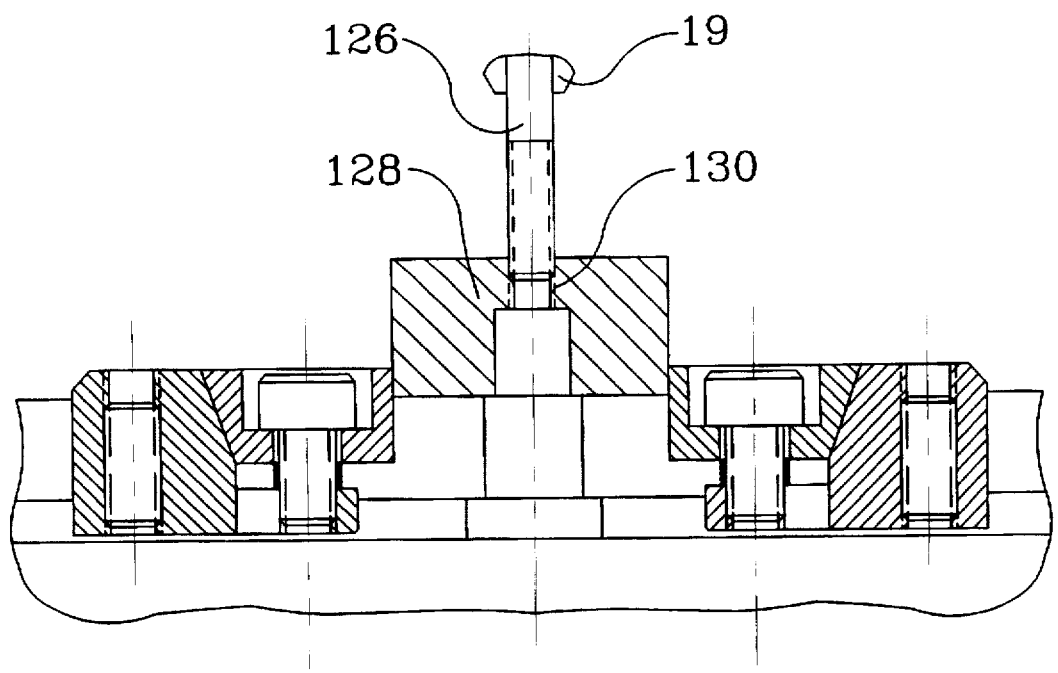
FIG. 10 is a fragmental sectional side view that illustrates testing of threaded specimens.

FIG. 10 is a fragmental sectional side view that illustrates testing of threaded specimens. In the case shown in FIG. 10, upper specimen 126 is in the form of a threaded stud which is clamped in collet chuck 19 of the tester. Lower specimen 128 is shown in the form of a solid block with a threaded opening 130. For testing, lower specimen 128 is fixed in bowl 22 so that threaded opening 130 is strictly coaxial with the longitudinal axis of upper specimen 126. The testing of the threaded specimens is carried out in the same manner as with flat-contact specimens, with the exception that after contact of upper specimen 126 with lower specimen 128 axial downward movement of upper specimen 126 is not discontinued, and both motors 58 and 62 continue to operate so that the friction force and torque are measured during screwing of upper specimen 126 into threaded opening 130 of lower specimen 128.

In both cases, testing may be conducted under dry or wet conditions.

In the case of the single-row coupling of FIGS. 7 and 8, the tester will operate in the same manner as in conjunction with the coupling of FIG. 6, with the exception that in relative motion of the upper specimen, e.g., threaded stud 126, with respect to lower specimen 128 having threaded opening 130 into which stud 126 is screwed, stud 126 will have only one degree of freedom, i.e., in the axial direction, and will be strictly coaxial with the respect to the axis of threaded opening 130. This means that no lateral components of the force will appear in testing. At the same time, the pitch error of the thread will be compensated by axial displacements. This will prevent overloading and damage of the thread and tooling.

RAMIFICATIONS AND SCOPE

Thus, it has been shown that the invention provides a universal tester for testing static and dynamic coefficients of friction, friction torque, friction force, adhesion force, abrasive and adhesive wear of the specimens, friction characteristics of thread, friction characteristics under cold and hot conditions, and stick-slip characteristics on one tester. Aforementioned parameters may be tested for specimens of different types and configurations. The tester is highly sensitive to displacements of the upper specimen in the axial direction and therefore makes it possible to measure characteristics of a stick-slip phenomena. The tester ensures full surface-to-surface contact of flat specimens. It is relative inexpensive to manufacture. The invention also provides a method of testing various friction characteristics with the use of the aforementioned tester.

Although the invention has been shown and described with reference to specific embodiments and steps of the method, it is understood that materials, configurations, dimensions of the parts and their arrangement, as well as the steps of the method should not be construed as limiting the scope of the application of the invention and that any changes and modifications are possible, provided they do not depart from the appended claims.

For example, bolts and screws can be used as upper specimens instead of this stud shown in FIG. 10. The upper specimen can be clamped in a three-jaw type chuck and the lower specimen can be fixed in a vacuum chuck, or any other clamping mechanism. The upper specimen may have a disk-like configuration and the lower specimen may be in the form of a rod. Both specimens may have any configuration necessary for testing. For example, they may be represented by specific parts of machines or instruments such as brake pads, etc. The bowl may incorporate a heater of any type for heating the lower specimen. The bowl may have a cooling chamber for testing friction under low-temperature conditions, etc. Testing may be performed with participation of a plurality of test specimens of one type having friction contact with one or several test specimens of another type.

We claim:

1. An apparatus for measuring friction and wear characteristics of test specimens having friction contact with each other, comprising:

a stationary rigid frame with guide means;

a carriage slidingly installed on said guide means;

a linear means for moving said carriage along said guide means;

a rotary drive means supported by said carriage and having an output member with means for fixation of a first test specimen, said first test specimen having a longitudinal axis;

a flexible coupling having an input member attached to said output member of said rotary drive means, an output member attached to said input member of said flexible coupling, and a flexible means that interconnects said input and output members of said flexible coupling, said output member of said flexible coupling having at least one degree of freedom, said flexible coupling being installed between said output member of said rotary drive means and said means for fixation of said first test specimen;

means for fixation of a second test specimen in a testing position, said means for fixation of a second test specimen being attached to said stationary rigid frame, said second test specimen having a longitudinal axis, said means for fixation of said first and second specimens being formed so that in said testing position said longitudinal axis of said first test specimen is parallel to said longitudinal axis of said second test specimen, said at least one degree of freedom of said flexible coupling being a degree of freedom in a direction of said longitudinal axis of said first test specimen; and a measuring system for measuring friction and wear characteristics of said test specimens in a friction contact.

2. The apparatus of claim 1 wherein said flexible means comprises a set of leaf springs, said input member having a pilot member, said output member having guiding means that slidingly receives said pilot member without backlash, so that said output member of said flexible coupling may freely move in the direction of said longitudinal axis of said first test specimen but cannot tilt with respect to said axis.

3. The apparatus of claim 1 wherein said coupling having three degrees of freedom for movement of said first test specimen when said first test specimen is fixed in said means for fixation of said first test specimen, said three degrees of freedom being a first degree of freedom in the direction of said longitudinal axis of said first test specimen, a second degree of freedom in a plane perpendicular to said longitudinal axis of said first specimen, and a third degree of freedom in said plane perpendicular to said second degree of freedom.

4. The apparatus of claim 3 further comprising a spacer for spacing said input member and output member of said flexible coupling from each other; said flexible means comprising a first flexible member and a second flexible member, said first flexible member connecting said input member of said flexible coupling to said spacer, and said second flexible member connecting said spacer to said output member of said flexible coupling.

5. The apparatus of claim 4 wherein said first flexible member comprising a first set of leaf springs and a second flexible member comprising a second set of leaf springs.

6. The apparatus of claim 4 wherein said means for fixation of said second test specimen comprises: a lower plate with means for leveling the plane of said lower plate, an interchangeable bowl with means for clamping said second test specimen in said testing position, and intermediate plate between said interchangeable and said lower plate for supporting said interchangeable bowl, said measuring system having a load cell capable of measuring friction forces and torques, said load cell being located between said lower plate and said intermediate plate.

7. The apparatus of claim 6 wherein said interchangeable bowl has an upper edge which is raised to define a space for receiving a liquid.

8. The apparatus of claim 4 wherein said linear means for moving said carriage includes a first stepper motor attached to said rigid frame, a lead screw installed in said rigid frame parallel to said guide means; and a nut engaged with said lead screw and attached to said carriage, said rotary drive means including a second stepper motor.

9. An apparatus for measuring friction and wear characteristics of test specimens having friction contact with each other, comprising:
- a stationary rigid frame with guide means;
- a carriage slidingly installed on said guide means;
- a linear means for moving said carriage along said guide means;
- a rotary drive means supported by said carriage and having an output member with means for fixation of a first test specimen, said first test specimen having a longitudinal axis;
- a flexible coupling having an input member attached to said output member of said rotary drive means, an output member attached to said input member of said flexible coupling, and a flexible means that interconnects said input and output members of said flexible coupling, said coupling having three degrees of freedom for movement of said first test specimen when said first test specimen is fixed in said means for fixation of said first test specimen, said three degrees of freedom being a first degree of freedom in a direction of said longitudinal axis of said first test specimen, a second degree of freedom in a plane perpendicular to said longitudinal axis of said first specimen, and a third degree of freedom in a plane perpendicular to said second degree of freedom, a spacer spacing said input member and output member of said flexible coupling from each other, said flexible means including a first flexible member and a second flexible member, said first flexible member connecting said input member of said flexible coupling to said spacer, and said second flexible member connecting said spacer to said output member of said flexible coupling;
- means for fixation of a second test specimen in a testing position, said means for fixation of a second test specimen being attached to said stationary rigid frame, said second test specimen having a longitudinal axis, said means for fixation of said first and second specimens being formed so that in said testing position said longitudinal axis of said first test specimen is parallel to said longitudinal axis of said second test specimen, said at least one degree of freedom of said flexible coupling being a degree of freedom in the direction of said longitudinal axis of said first test specimen; and
- a measuring system for measuring friction and wear characteristics of said test specimens in a friction contact.

10. The apparatus of claim 9 wherein said first flexible member includes a first set of leaf springs and said second flexible member includes a second set of leaf springs.

11. The apparatus of claim 10 wherein said means for fixation of said second test specimen includes: a lower plate with means for leveling a plane of said lower plate, an interchangeable bowl with means for clamping said second test specimen in said testing position, and intermediate plate between said interchangeable and said lower plate for supporting said interchangeable bowl, said measuring system having a load cell for measuring forces and torques, said load cell being located between said lower plate and said intermediate plate, said interchangeable having an upper edge which is raised to define a space for receiving a test oil.

12. The apparatus of claim 11 wherein said measuring system is formed so that it measures said friction and wear characteristics selected from the group consisting of a coefficient of friction, friction torque, friction force, abrasive wear, friction characteristics of thread, friction characteristics under cold and hot conditions, and stick-slip characteristics.

13. A method for measuring friction and wear characteristics of test specimens having friction contact with each other, comprising the steps of:
- providing a tester having means for installing a first test specimen rotationally and moveably in an axial direction and means for installing a second test specimen stationary with respect to said first test specimen, said first test specimen having a contact surface and a longitudinal axis, said second test specimen having a contact surface and a longitudinal axis parallel to said longitudinal axis of said first test specimen, said tester having means for measuring said friction and wear characteristics;
- causing rotation of said first test specimen and bringing said contact surface of said first test specimen into contact with said contact surface of said second test specimen;
- applying a force to said first test specimen when it rotates and is in said contact with said second test specimen; and
- transmitting said force and said torque from said first test specimen to said second test specimen via a flexible coupling that has at least one degree of freedom in the direction of said longitudinal axis of said first test specimen; and
- measuring said friction and wear characteristics.

14. The apparatus of claim 13 wherein said coupling has three degrees of freedom for movement of said first test specimen, said three degrees of freedom being a first degree of freedom in the direction of said longitudinal axis of said first test specimen, a second degree of freedom in a plane perpendicular to said longitudinal axis of said first specimen, and a third degree of freedom in a plane perpendicular to said second degree of freedom.

* * * * *